(12) United States Patent
Ashby et al.

(10) Patent No.: US 8,050,741 B2
(45) Date of Patent: Nov. 1, 2011

(54) DEVICE AND METHOD FOR FACILITATING HEMOSTASIS OF A BIOPSY TRACT

(75) Inventors: Mark Ashby, Laguna Niguel, CA (US); Vaughn P. Whalen, Dana Point, CA (US); Eduardo Chi Sing, Dana Point, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1449 days.

(21) Appl. No.: 11/019,971

(22) Filed: Dec. 21, 2004

(65) Prior Publication Data

US 2005/0113737 A1    May 26, 2005

Related U.S. Application Data

(63) Continuation of application No. 09/960,389, filed on Sep. 24, 2001, now Pat. No. 6,846,320, which is a continuation of application No. 09/382,160, filed on Aug. 24, 1999, now abandoned, which is a continuation-in-part of application No. 09/247,880, filed on Feb. 10, 1999, now Pat. No. 6,086,607, which is a continuation-in-part of application No. 09/071,670, filed on May 1, 1998, now Pat. No. 6,071,301.

(51) Int. Cl.
*A61B 6/00* (2006.01)
*A61B 10/00* (2006.01)

(52) U.S. Cl. ......... 600/431; 600/432; 600/564; 600/566

(58) Field of Classification Search .................. 600/431, 600/432, 562–568, 433
See application file for complete search history.

(56) References Cited

U.S. PATENT DOCUMENTS 581,235 A    4/1897    Kenyon
(Continued)

FOREIGN PATENT DOCUMENTS

EP    0032826    7/1981
(Continued)

OTHER PUBLICATIONS

Tobin et al. "Plugged Liver Biopsy in Patients with Impaired Coagulation". Digestive Diseases and Science, vol. 34, No. 1 (Jan. 1989) pp. 13-15.*

(Continued)

*Primary Examiner* — Max Hindenburg
*Assistant Examiner* — Jonathan M Foreman
(74) *Attorney, Agent, or Firm* — Seager, Tufte & Wickhem, LLC

(57) ABSTRACT

A biopsy cannula and a delivery catheter are configured to deliver one or more absorbable sponge pledgets to a biopsy site after removal of one or more tissue samples from the site. The delivery catheter allows a large amount of hydrated sponge material to be delivery to the biopsy site to facilitate hemostasis. One example of the delivery catheter includes a closed distal end, a side port, a tapered section, and an enlarged proximal portion for receiving the pledget. The side port of the delivery catheter is arranged to delivery the pledget through the side port of the biopsy cannula. In order to fill a relatively large biopsy site where multiple tissue samples have been taken in a radial pattern, the biopsy cannula is rotated and additional pledgets are delivered to the biopsy site at different radial locations. The absorbable sponge pledget may also be used as a marker for location of the biopsy site at a later time.

17 Claims, 9 Drawing Sheets

U.S. PATENT DOCUMENTS

| | | |
|---|---|---|
| 1,578,517 A | 3/1926 | Hein |
| 2,086,580 A | 7/1937 | Shirley |
| 2,370,319 A | 2/1945 | Lippincott |
| 2,492,458 A | 12/1946 | Bering, Jr. |
| 2,465,357 A | 3/1949 | Correll |
| 2,507,244 A | 5/1950 | Correll |
| 2,558,395 A | 6/1951 | Studer |
| 2,597,011 A | 5/1952 | MacMasters et al. |
| 2,680,442 A | 6/1954 | Linzmayer |
| 2,761,446 A | 9/1956 | Reed |
| 2,814,294 A | 11/1957 | Figge |
| 2,824,092 A | 2/1959 | Thompson |
| 2,874,776 A | 2/1959 | Hooe |
| 2,899,362 A | 8/1959 | Sieger, Jr. et al. |
| 2,997,195 A | 8/1961 | Yeun |
| 3,157,524 A | 11/1964 | Artandi |
| 3,358,689 A | 12/1967 | Higgins |
| 3,411,505 A | 11/1968 | Nobis |
| 3,703,174 A | 11/1972 | Smith |
| 3,724,465 A | 4/1973 | Duchane |
| 3,736,939 A | 6/1973 | Taylor |
| 3,950,363 A * | 4/1976 | Bundy ................. 549/463 |
| 4,000,741 A | 1/1977 | Binard et al. |
| 4,098,728 A | 7/1978 | Rosenblatt |
| 4,211,323 A | 7/1980 | Olsen |
| 4,218,155 A | 8/1980 | Weidner |
| 4,219,026 A | 8/1980 | Layton |
| 4,224,945 A | 9/1980 | Cohen |
| 4,238,480 A | 12/1980 | Sawyer |
| 4,292,972 A | 10/1981 | Pawelchak |
| 4,323,072 A | 4/1982 | Rosenbluth et al. |
| 4,340,066 A | 7/1982 | Shah |
| 4,390,018 A | 6/1983 | Zuloowski |
| 4,404,970 A | 9/1983 | Sawyer |
| 4,405,314 A | 9/1983 | Copi |
| 4,515,637 A | 5/1985 | Cioca |
| 4,573,576 A | 3/1986 | Krol |
| 4,587,969 A | 5/1986 | Gillis |
| 4,588,395 A | 5/1986 | Lemelson |
| 4,591,094 A | 5/1986 | Morris |
| 4,619,261 A | 10/1986 | Guerriero |
| 4,619,913 A | 10/1986 | Luck et al. |
| 4,644,649 A | 2/1987 | Seaman et al. |
| 4,645,488 A | 2/1987 | Matukas |
| 4,699,616 A | 10/1987 | Norwak |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,832,688 A | 5/1989 | Sagae et al. |
| 4,836,204 A | 6/1989 | Landymore et al. |
| 4,839,204 A | 6/1989 | Yoshino |
| 4,850,960 A | 7/1989 | Grayzel |
| 4,852,568 A | 8/1989 | Kensey |
| 4,869,143 A | 9/1989 | Merrick |
| 4,890,612 A | 1/1990 | Kensey |
| 4,900,303 A | 2/1990 | Lemelson |
| 4,929,246 A | 5/1990 | Sinofaky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,049,138 A | 9/1991 | Chevalier et al. |
| 5,053,046 A | 10/1991 | Janese |
| 5,061,274 A | 10/1991 | Kensey |
| 5,080,655 A | 1/1992 | Haaga |
| 5,106,376 A | 4/1992 | Mononen et al. |
| 5,108,421 A | 4/1992 | Fowler |
| 5,129,889 A | 7/1992 | Hahn |
| 5,160,323 A | 11/1992 | Andrew |
| 5,163,904 A | 11/1992 | Lampropoulos et al. |
| 5,167,624 A | 12/1992 | Butler et al. |
| 5,192,290 A | 3/1993 | Hilal |
| 5,192,300 A | 3/1993 | Fowler |
| 5,192,301 A | 3/1993 | Kamiya et al. |
| 5,195,988 A | 3/1993 | Haaga |
| 5,219,899 A | 6/1993 | Panster et al. |
| 5,220,926 A | 6/1993 | Jones |
| 5,221,259 A | 6/1993 | Weldon et al. |
| 5,222,974 A | 6/1993 | Kensey et al. |
| 5,232,453 A | 8/1993 | Plass et al. |
| 5,242,683 A | 9/1993 | Klaveness |
| 5,254,105 A | 10/1993 | Haaga |
| 5,275,616 A | 1/1994 | Fowler |
| 5,282,827 A | 2/1994 | Kensey et al. |
| 5,292,309 A | 3/1994 | Van Tassel et al. |
| 5,299,581 A | 4/1994 | Donnell et al. |
| 5,310,407 A | 5/1994 | Casale |
| 5,320,639 A | 6/1994 | Rudnick |
| 5,322,515 A | 6/1994 | Karas et al. |
| 5,325,857 A | 7/1994 | Nabai et al. |
| 5,334,216 A | 8/1994 | Vidal et al. |
| 5,342,388 A | 8/1994 | Toller |
| 5,350,399 A | 9/1994 | Erlebacher et al. |
| 5,352,211 A | 10/1994 | Merskelly |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammerslag |
| 5,385,550 A | 1/1995 | Su et al. |
| 5,388,588 A | 2/1995 | Nabai et al. |
| 5,391,183 A | 2/1995 | Janzen et al. |
| 5,399,361 A | 3/1995 | Song et al. |
| 5,417,699 A | 5/1995 | Klein |
| 5,419,765 A | 5/1995 | Weldon et al. |
| 5,431,639 A | 7/1995 | Shaw |
| 5,437,292 A | 8/1995 | Kipshidze |
| 5,437,631 A | 8/1995 | Janzen |
| 5,441,517 A | 8/1995 | Kensey et al. |
| 5,443,481 A | 8/1995 | Lee |
| 5,447,502 A | 9/1995 | Haaga |
| 5,458,570 A | 10/1995 | May, Jr. |
| 5,462,194 A | 10/1995 | Barawell |
| 5,467,780 A | 11/1995 | Nabai et al. |
| 5,478,352 A | 12/1995 | Fowler |
| 5,479,936 A * | 1/1996 | Nabai et al. ................. 600/567 |
| 5,486,195 A | 1/1996 | Myers |
| 5,490,736 A | 2/1996 | Haber |
| 5,507,279 A | 4/1996 | Fortune |
| 5,522,840 A | 6/1996 | Krajicek |
| 5,522,850 A | 6/1996 | Yomtov et al. |
| 5,526,822 A | 6/1996 | Burbank et al. |
| 5,527,332 A | 6/1996 | Clement |
| 5,529,577 A | 6/1996 | Hammerslag |
| 5,540,715 A | 7/1996 | Katseros et al. |
| 5,542,914 A | 8/1996 | Van Iten |
| 5,545,175 A | 8/1996 | Abidin et al. |
| 5,545,178 A | 8/1996 | Kensey et al. |
| 5,554,108 A | 9/1996 | Browning et al. |
| 5,558,853 A | 9/1996 | Quay |
| 5,571,168 A | 11/1996 | Toro |
| 5,591,204 A | 1/1997 | Janzen et al. |
| 5,591,205 A | 1/1997 | Fowler |
| 5,601,207 A | 2/1997 | Paczonay |
| 5,601,601 A | 2/1997 | Tal et al. |
| 5,601,602 A | 2/1997 | Fowler |
| 5,601,603 A | 2/1997 | Illi |
| 5,620,461 A | 4/1997 | Muijs Van De Moer |
| 5,637,096 A * | 6/1997 | Yoon ................. 604/158 |
| 5,645,566 A | 7/1997 | Brenneman et al. |
| 5,645,849 A | 7/1997 | Pruss et al. |
| 5,649,547 A | 7/1997 | Ritchart et al. |
| 5,653,730 A | 8/1997 | Hammerslag |
| 5,665,107 A | 9/1997 | Hammerslag |
| 5,674,346 A | 10/1997 | Kundel |
| 5,676,689 A | 10/1997 | Kensey |
| 5,681,279 A | 10/1997 | Roper et al. |
| 5,707,393 A | 1/1998 | Kensey et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,827,218 A | 10/1998 | Nguyen et al. |

| | | | |
|---|---|---|---|
| 5,830,130 | A | 11/1998 | Janzen et al. |
| 5,858,008 | A | 1/1999 | Capaccio |
| 5,861,004 | A | 1/1999 | Kensey et al. |
| 5,868,762 | A | 2/1999 | Cragg et al. |
| 5,902,310 | A | 5/1999 | Foerster et al. |
| 5,931,165 | A | 8/1999 | Reich et al. |
| 5,984,950 | A | 11/1999 | Cragg et al. |
| 6,007,563 | A | 12/1999 | Nash et al. |
| 6,027,471 | A | 2/2000 | Fallon et al. |
| 6,027,482 | A | 2/2000 | Imbert |
| 6,033,427 | A | 3/2000 | Lee |
| 6,056,768 | A | 5/2000 | Cates et al. |
| 6,063,061 | A | 5/2000 | Wallace et al. |
| 6,066,325 | A | 5/2000 | Wallace et al. |
| 6,071,300 | A | 6/2000 | Brenneman et al. |
| 6,071,301 | A | 6/2000 | Cragg et al. |
| 6,086,607 | A | 7/2000 | Cragg et al. |
| 6,090,130 | A | 7/2000 | Nash et al. |
| 6,126,675 | A | 10/2000 | Shchervinsky et al. |
| 6,161,034 | A | 12/2000 | Burbank et al. |
| 6,162,192 | A | 12/2000 | Cragg et al. |
| 6,183,497 | B1 | 2/2001 | Sing et al. |
| 6,197,327 | B1 | 3/2001 | Harrison et al. |
| 6,200,328 | B1 | 3/2001 | Cragg et al. |
| 6,228,049 | B1 * | 5/2001 | Schroeder et al. ......... 604/93.01 |
| 6,228,055 | B1 * | 5/2001 | Foerster et al. ............... 604/116 |
| 6,315,753 | B1 | 11/2001 | Cragg |
| 6,325,789 | B1 | 12/2001 | Janzen et al. |
| 6,368,341 | B1 * | 4/2002 | Abrahamson ................ 606/213 |
| 6,371,974 | B1 | 4/2002 | Brenneman et al. |
| 6,440,151 | B1 | 8/2002 | Cragg et al. |
| 6,440,153 | B2 | 8/2002 | Cragg et al. |
| 6,447,534 | B2 | 9/2002 | Cragg et al. |
| 6,503,222 | B2 | 1/2003 | Lo |
| 6,527,734 | B2 | 3/2003 | Cragg et al. |
| 6,540,735 | B1 | 4/2003 | Ashby et al. |
| 6,544,236 | B1 | 4/2003 | Cragg et al. |
| 6,547,806 | B1 | 4/2003 | Ding |
| 6,585,680 | B2 | 7/2003 | Bugge |
| 6,610,026 | B2 | 8/2003 | Cragg et al. |
| 2002/0002889 | A1 | 1/2002 | Ashby et al. |
| 2002/0016612 | A1 | 2/2002 | Ashby et al. |
| 2002/0038133 | A1 | 3/2002 | Sing et al. |
| 2002/0042378 | A1 | 4/2002 | Reich et al. |
| 2002/0062104 | A1 | 5/2002 | Ashby et al. |
| 2002/0156495 | A1 | 10/2002 | Brenneman et al. |
| 2003/0028140 | A1 | 2/2003 | Greff et al. |
| 2003/0088269 | A1 | 5/2003 | Ashby |
| 2003/0088271 | A1 | 5/2003 | Cragg et al. |
| 2003/0120258 | A1 | 6/2003 | Ashby et al. |
| 2003/0135237 | A1 | 7/2003 | Cragg et al. |
| 2004/0019328 | A1 | 1/2004 | Sing et al. |
| 2004/0019330 | A1 | 1/2004 | Ashby |

FOREIGN PATENT DOCUMENTS

| | | |
|---|---|---|
| EP | 0476178 | 3/1992 |
| EP | 0482350 | 4/1992 |
| EP | 0557963 | 2/1993 |
| EP | 0637432 B1 | 9/1994 |
| EP | 0637431 | 11/1994 |
| FR | 2641692 | 7/1990 |
| GB | 1509023 | 4/1978 |
| GB | 1569660 | 6/1980 |
| SU | 782814 | 11/1980 |
| SU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 95/32679 | 12/1995 |
| WO | WO 96/08208 | 3/1996 |
| WO | WO 96/24290 | 8/1996 |
| WO | WO 97/07934 | 3/1997 |
| WO | WO 97/09934 | 3/1997 |
| WO | WO 98/06346 | 2/1998 |
| WO | WO 99/66834 | 12/1999 |
| WO | WO 2004/093649 | 11/2004 |

OTHER PUBLICATIONS

Allison, D., "Percutaneous Liver Biopsy and Track Embolization with Steel Coils," *Radiology*, vol. 169, 1998, p. 261.

Berman, Howard L., "Guided Direct Antegrade Puncture of the Superficial Femoral Artry," *American Ray Society Roentgen*, Sep. 1986, p. 632.

Berman, Howard L., "Modification of the Cope Drainage Catheter to Facilitate Placement," *American Ray Society Roentgen*, Jan. 1986, pp. 146, 169.

Bryne, J., "Endovascular Treatments for Intracranial Anuerysms," *The British Journal of Radiology*, 1996, pp. 98, 891.

Chuang, V., "Sheath Needle for Liver Biopsy in High-Risk Patience," *Radiology*, vol. 166, 1988, p. 261.

Correll, John T., "Certain Properties of a New Physiologically Absorbable Sponge," *Research Laboratories of the Upjohn Company*, 1944, p. 233.

Correll, John T., "Biologic Investigations of New Absorbable Sponge," *Research Laboratories of the Upjohn Company*, 1945, p. 585.

Di Seni, Ricardo, "Part 1, Embolotherapy: Agents, Equipment, and Techniques," *Vascular Embolotherapy*, vol. 4, p. 29.

Fandrich, C., "Small Guage Gelfoam Plug Liver Biopsy in High Risk Patients," *Australian Radiology*, vol. 40, 1996, p. 230. High Risk Patients, *Australian Radiology*, vol. 40, 1996, p. 230.

Foran, JPM, "Early Mobilization After Percutaneous Cardiac Catheterisation Using Collagen Plug (Vasoseal) Maemostatis," *BRHeart*, vol. 69, 1993, p. 424.

Gibbs, JSR, "Femoral Arterial Hemostasis Using a Collagen Plug After Coronary Artery Stent Implantation," *J. Interventional Card*, vol. 5, 1992, p. 85.

*Journal of Interventional Cardiology*, vol. 5, No. 2, Jun. 1992.

Kassell, N., "Size of Intracranial Aneurysm," vol. 12, No. 3, 1983.

Kiemeneij, F., "Improved Anticoagulation Management after Palmaz Schatz Coronary Stent Implantation by Sealing the Arterial Puncture Site with Vascular Hemostasis Device," *Catheterization and Cardiovascular Diagnosis*, vol. 30, 1995, p. 1685.

Kussmaul, W.G., "Rapid Arterial Hemostasis . . . Randomized Trial of a Novel Hemostatic Device," *J. Am. Coll. Card.*, vol. 25, 1995, p. 1685.

"Gelfoam Sterile Sponge, Sterile Powder and Sterile Film," *Pharmacia & Upjohn Manufacturer Brochure*, May 1997, p. 1.

"Gelfoam Sterile Powder," *Pharmacia & Upjohn Manufacturer Brochure*, Feb. 1996.

"Gelfoam Sterile Powder," *Pharmacia & Upjohn Manufacturer Brochure*, Mar. 1996.

"Gelfoam Sterile Sponge, Sterile Powder and Sterile Film," *Pharmacia & Upjohn Manufacturer Specification*, Nov. 1996, p. 1.

Riley, S.A., "Percutaneous Liver Biopsy with Plugging of Needle Track: a Safe Method for Use in Patients with Impaired Coagulation," *The Lancet*, 1964, p. 436.

Saddekni, S., M.D., "Antegrade Cathererization of the Superficial Femoral Artery," *Radiology*, 1985, p. 531.

Sanborn, T., "Multicenter Randomized Trial Comparing Perutaneous Collagen Hemostasis Device with Conventional Manual Compression after Diagnostic Angiography and Angioplasty," *J. Am. Coll. Card.*, vol. 22, 1993, p. 1273.

Scharader, R., "Collagen Appl.," *Catheterization & Cardiovascular Diagnosis*, 1992, p. 298.

Schievink, "Intracranial Aneurysms," *The New England Journal of Medicine; Review Articles*, Jan. 2, 1997.

Silber, S., "Rapid Hemostasis of Arterial Puncture Sites with Collagen in Patients Undergoing Diagnostic Interventional Cardiac Catherterization," *Clinical Cardiology*, vol. 20, 1997, p. 981.

Smith, T., "Percutaneous Transhepatic Liver Biopsy with Tract Embolization," *Radiology*, vol. 198, 1996, p. 769.

Szikora, I., "Combined Use of Stents and Cells to Treat Experimental Wide-Necked Carotid Aneurysms: Preliminary Results," *AJNR AM Neuroradiol*, Jun. 1994, p. 1091.

Szikora, I., "Endovascular Treatment of Experimental Anuerysms with Liquid Polymers," vol. 38, No. 2, Feb. 1996.

Turjman, F., "Combined Stent Implantation & Endosacular Coil Placement for Treatment of Experimental Wide-Necked Aneurysms," *AJNRAM J. Neuroradio*, Jun. 1994, p. 1087.

Vogelzang, Robert L., "A Modified Cope Introducing Dilator to Allow Straight Guide Wire Introduction," *American Roantigen Ray Society*, Feb. 1986, p. 381.

Yoshimoto, Y., "Cerebral Anuerysms Unrelated to Arterial Bifurcations," *Acta Neurochir (Wien)*, 1996, 138:958-964.

Zins, M., "US-Guided Percutaneous Liver Biopsy with Plugging of the Needle Track," *Radiology*, vol. 187, 1992, p. 841.

Our Pending Applications (125) Ashby, Mark et al; U.S. Appl. No. 10/287,922, filed Nov. 4, 2002; entitled: Apparatus and Method for Inhibiting Blood Loss.

(130) Ashby, Mark et al; U.S. Appl. No. 10/069,107, filed Dec. 16, 2002; entitled: Device and Method for Determining a Depth of an Incision.

(144) Ashby, Mark et al; U.S. Appl. No. 10/278,710, filed Oct. 22, 2002; entitled: "System and Method for Facilitating Hemostasis of Blood Vessel Punctures With Absorbable Sponge".

(152) Ashby, Mark et al; U.S. Appl. No. 10/334,770, filed Dec 31, 2002; entitled: "Improved System and Method for Facilitating Hemostasis with Absorbable Sponge".

(159) Ashby, Mark et al; U.S. Appl. No. 10/462,065, filed Jun. 12, 2003; entitled: "Enhanced Bleed Back System".

(160) Ashby, Mark et al, U.S. Appl. No. 10/462,064, filed Jun. 12, 2003; entitled: "Release Mechanism".

Ashby, Mark et al; U.S. Appl. No. 10/461,587, filed: Jun. 12, 2003; entitled: "Dissolvable Closure Device".

(162) Ashby, Mark et al; U.S. Appl. No. 10/461,035, filed Jun. 13, 2003; entitled: "System and Method for Delivering Hemostasis Promoting Material to a Blood Vessel Puncture Site Using a Cannula".

(163) Ashby, Mark et al; U.S. Appl. No. 10/461,006, filed Jun. 13, 2003; entitled: "System and Method for Delivering Hemostasis Promoting Material to a Blood Vessel Puncture with a Staging Tube".

(164) Ashby, Mark et al; U.S. Appl. No. 10/460,859, filed Jun. 12, 2003; entitled: "Hemostatic Device Including a Capsule".

(187) Ashby, Mark et al; U.S. Appl. No. 10/732,441; filed Dec. 9, 2003; entitled: "Pledget-Handling System and Method for Delivering Hemostasis Promoting Material to a Blood Vessel Puncture Site by Fluid Pressure".

(190) Ashby, Mark et al; U.S. Appl. No. 10/754,824; filed Jan. 9, 2004; entitled: "Sheath-Mounted Arterial Plug Delivery Device".

(204) Ashby et al ; U.S. Appl. No. 10/959,898, filed Dec. 5, 2004; entitled: "Methods for Sterilizing Cross-Linked Gelatin Compositions".

(203) Ashby et al; U.S. Appl. No. 10/978,321, filed Oct. 29, 2004; entitled: "Absorbable Sponge With Contrasting Agent".

* cited by examiner

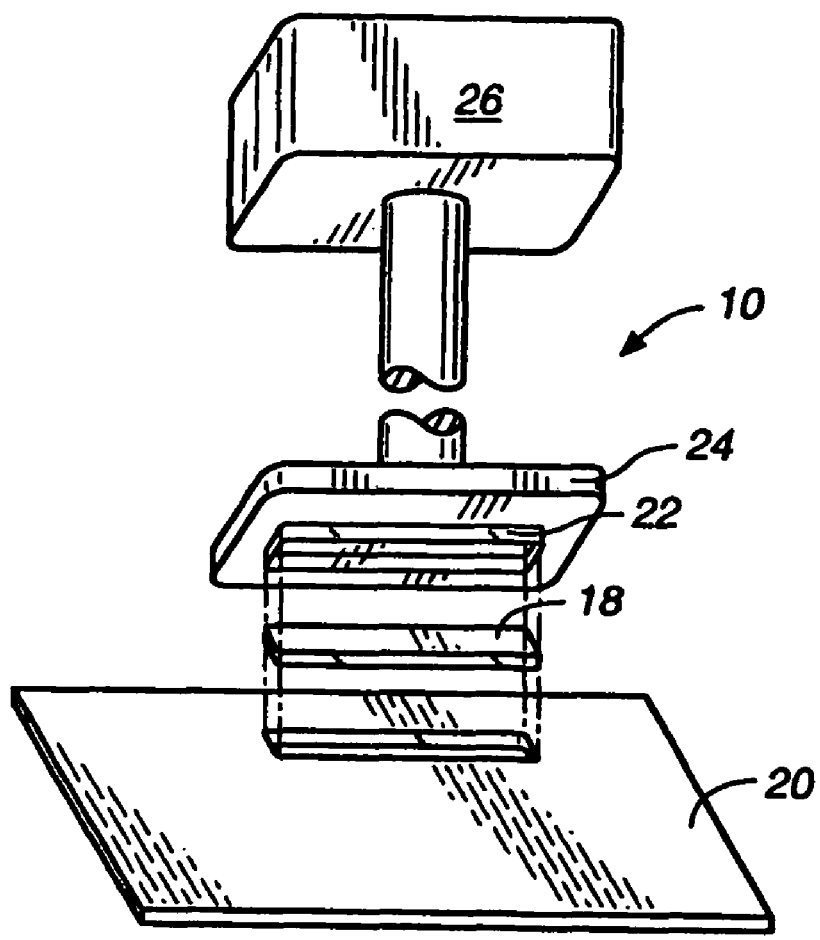
FIG._1

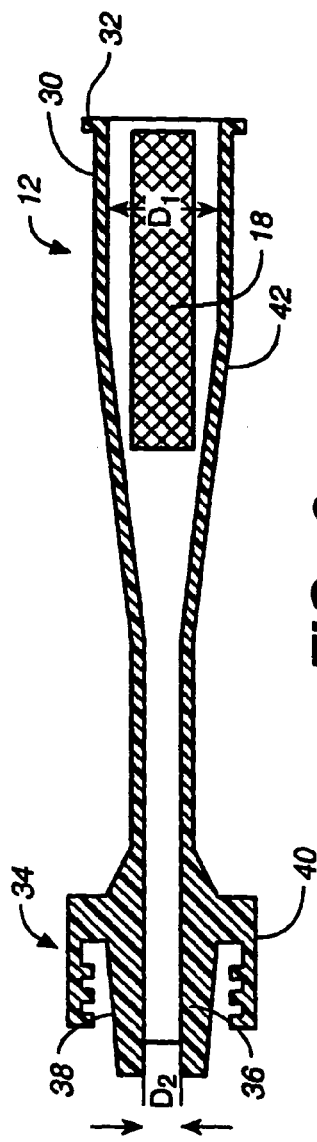
FIG._2
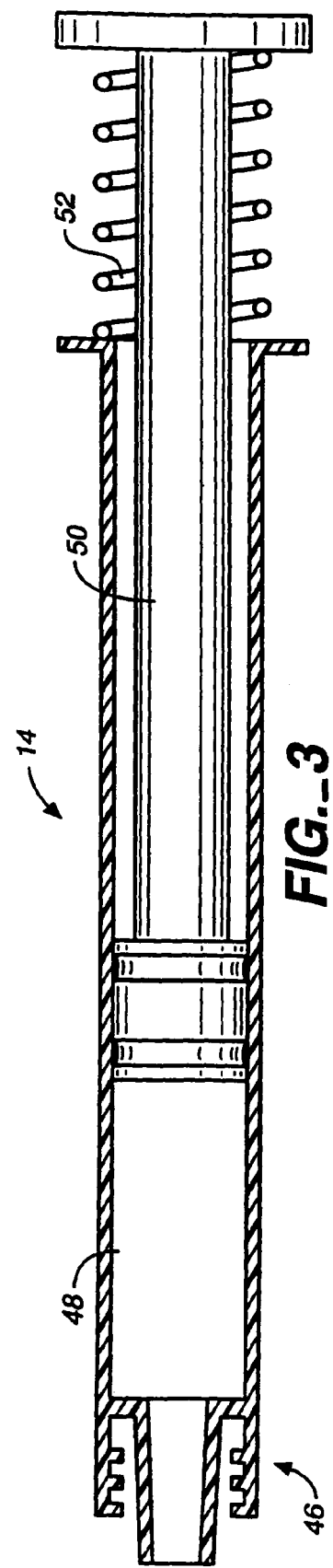
FIG._3

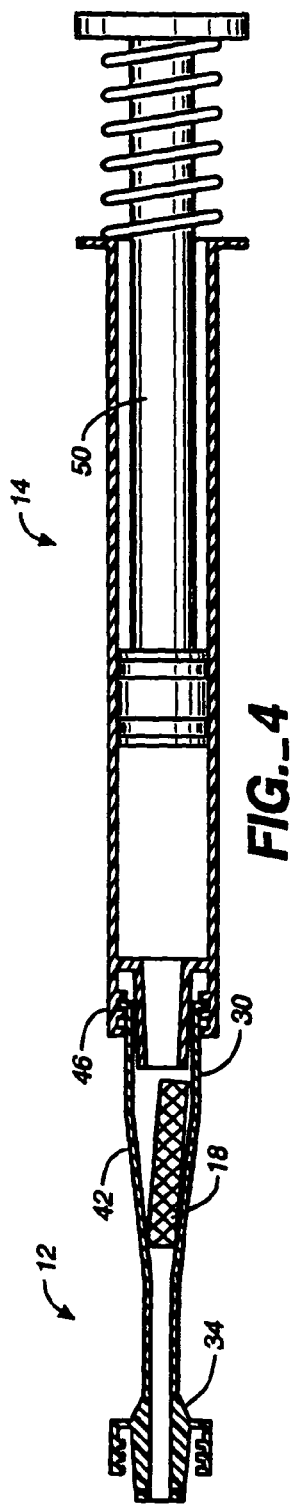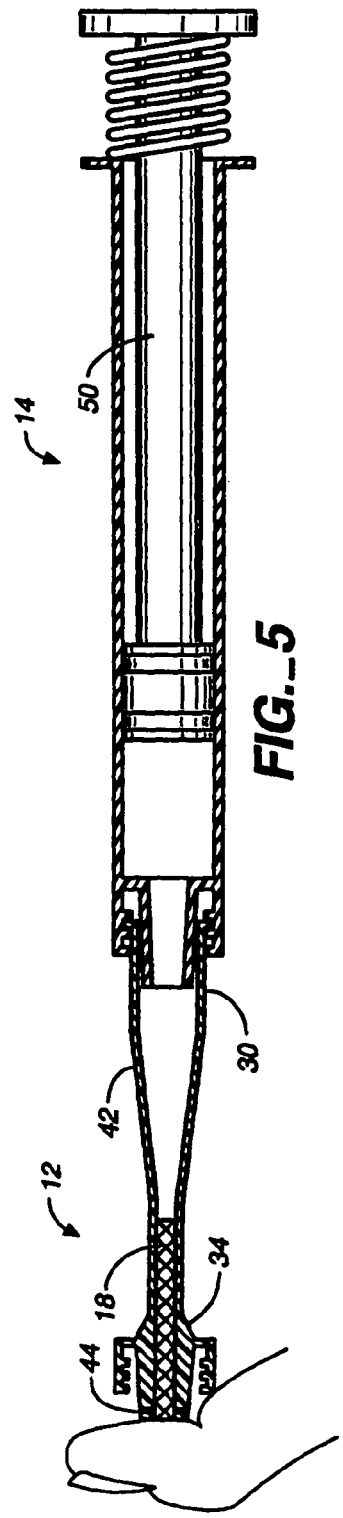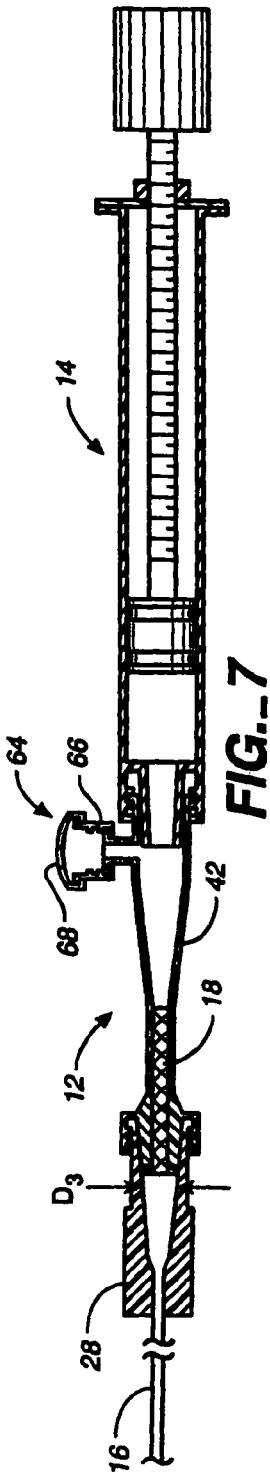

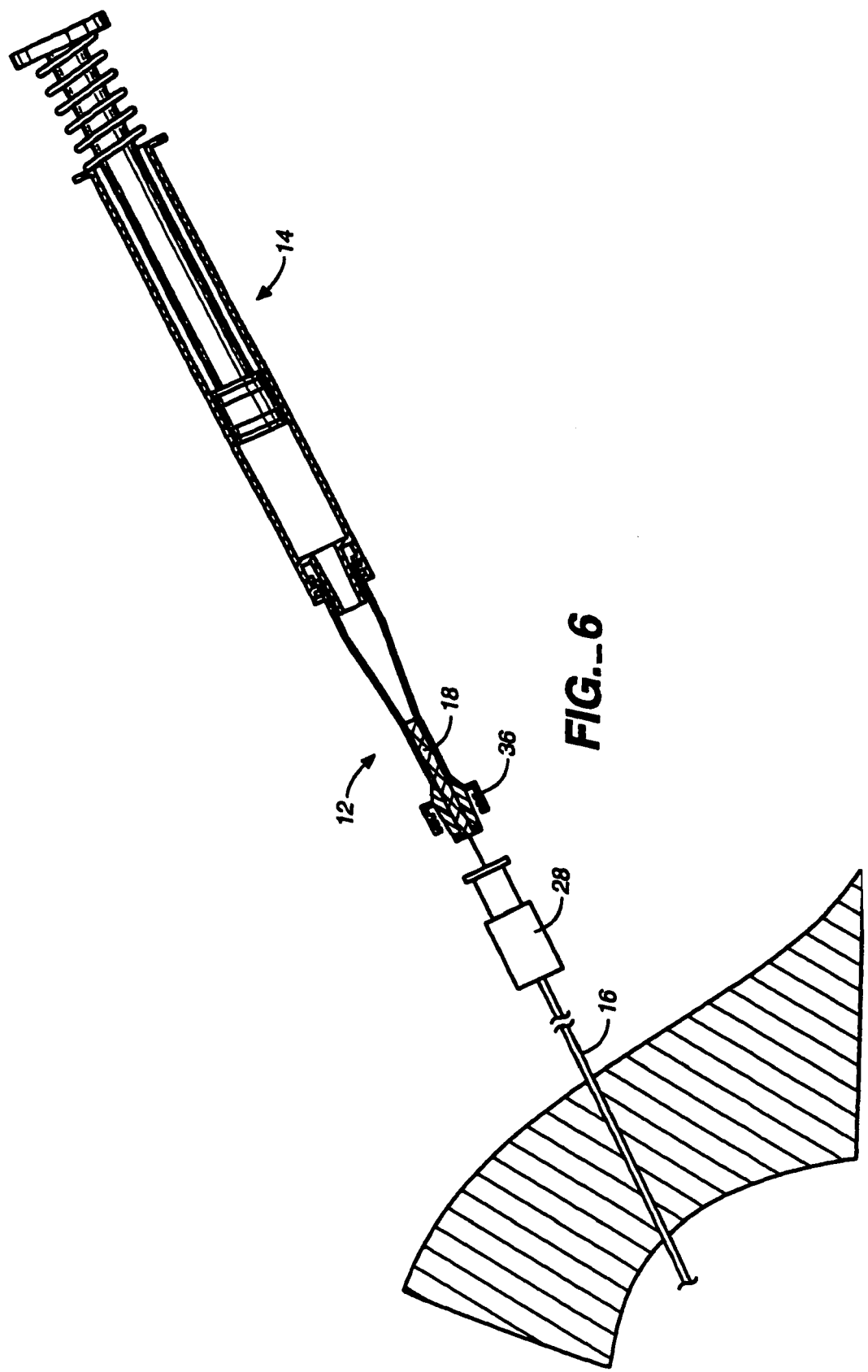
FIG._6

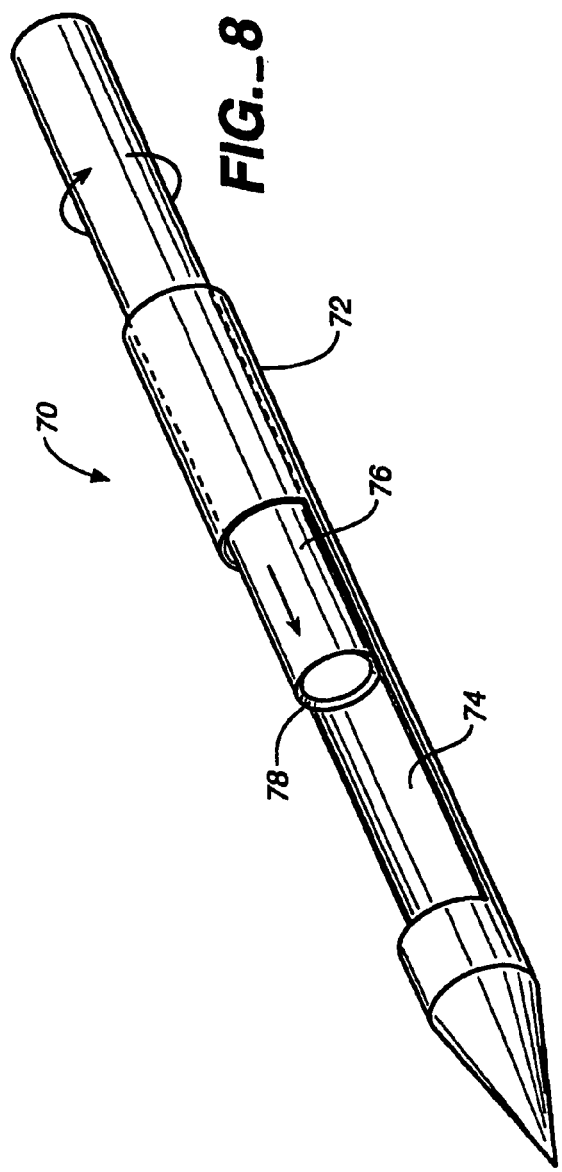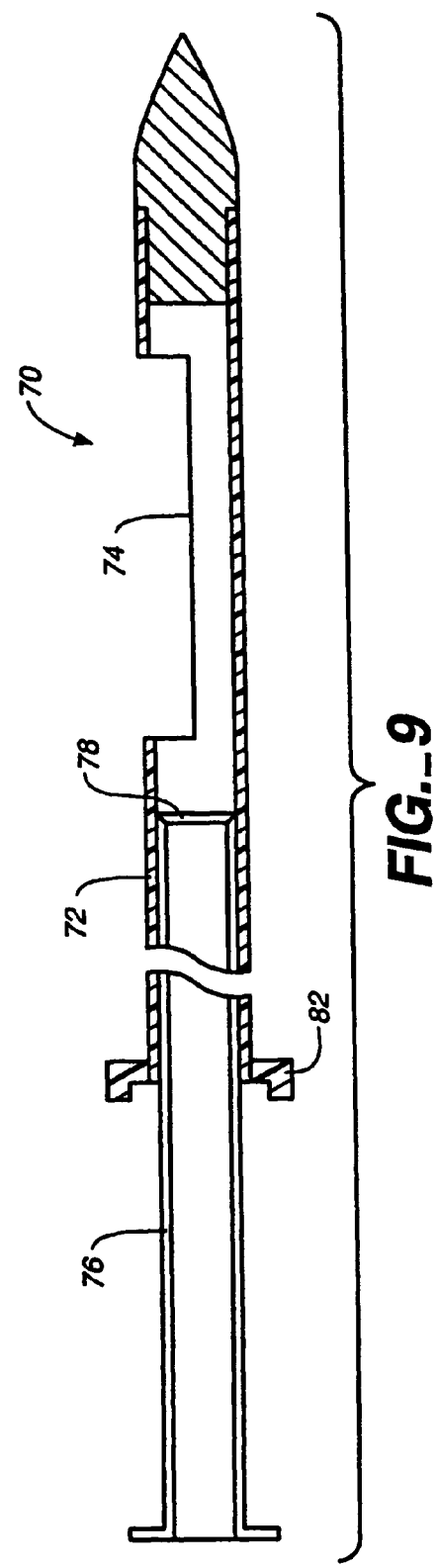

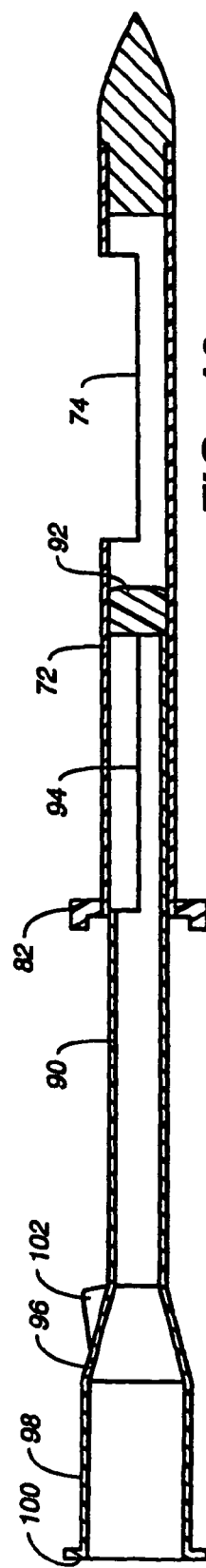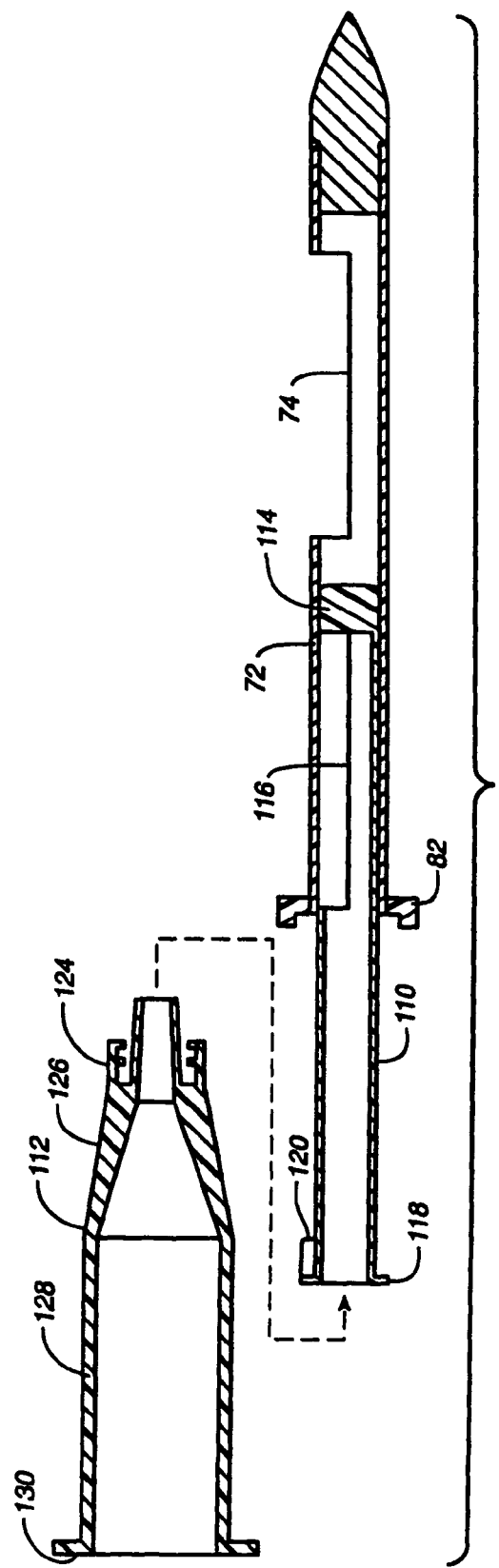

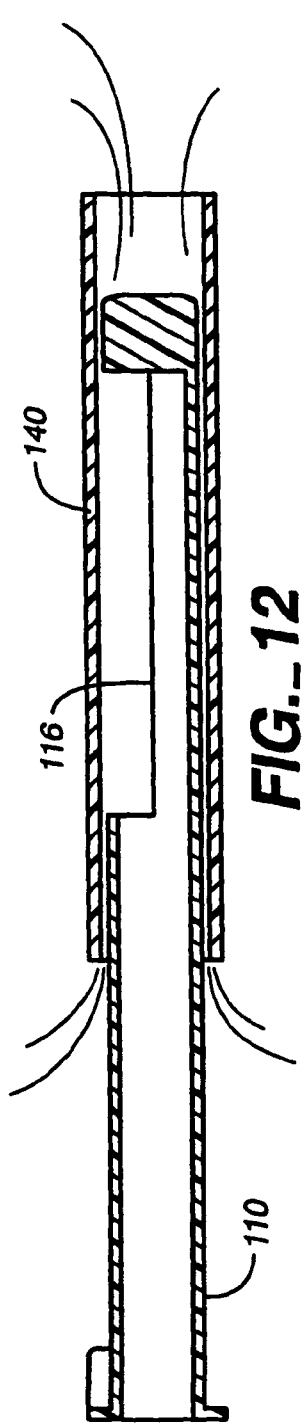
FIG._12
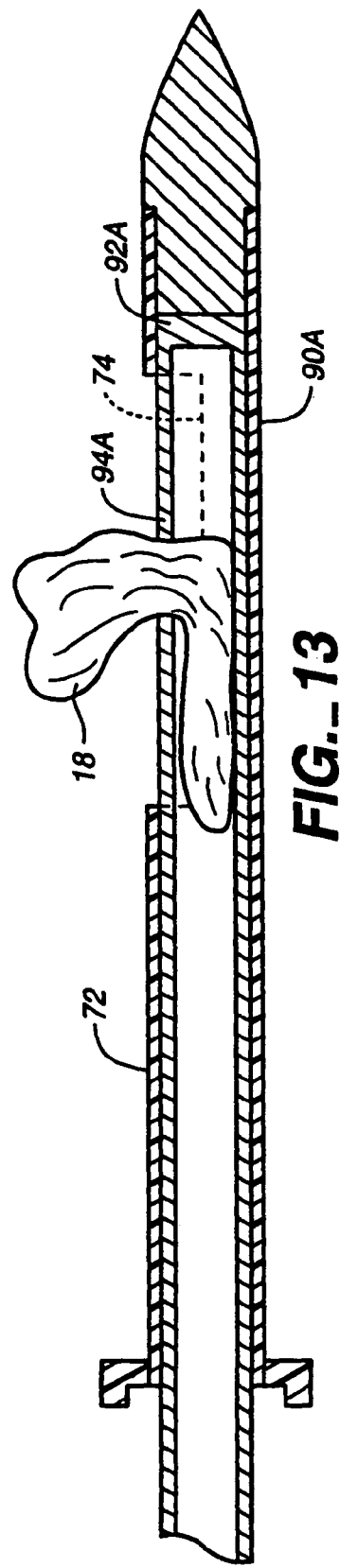
FIG._13

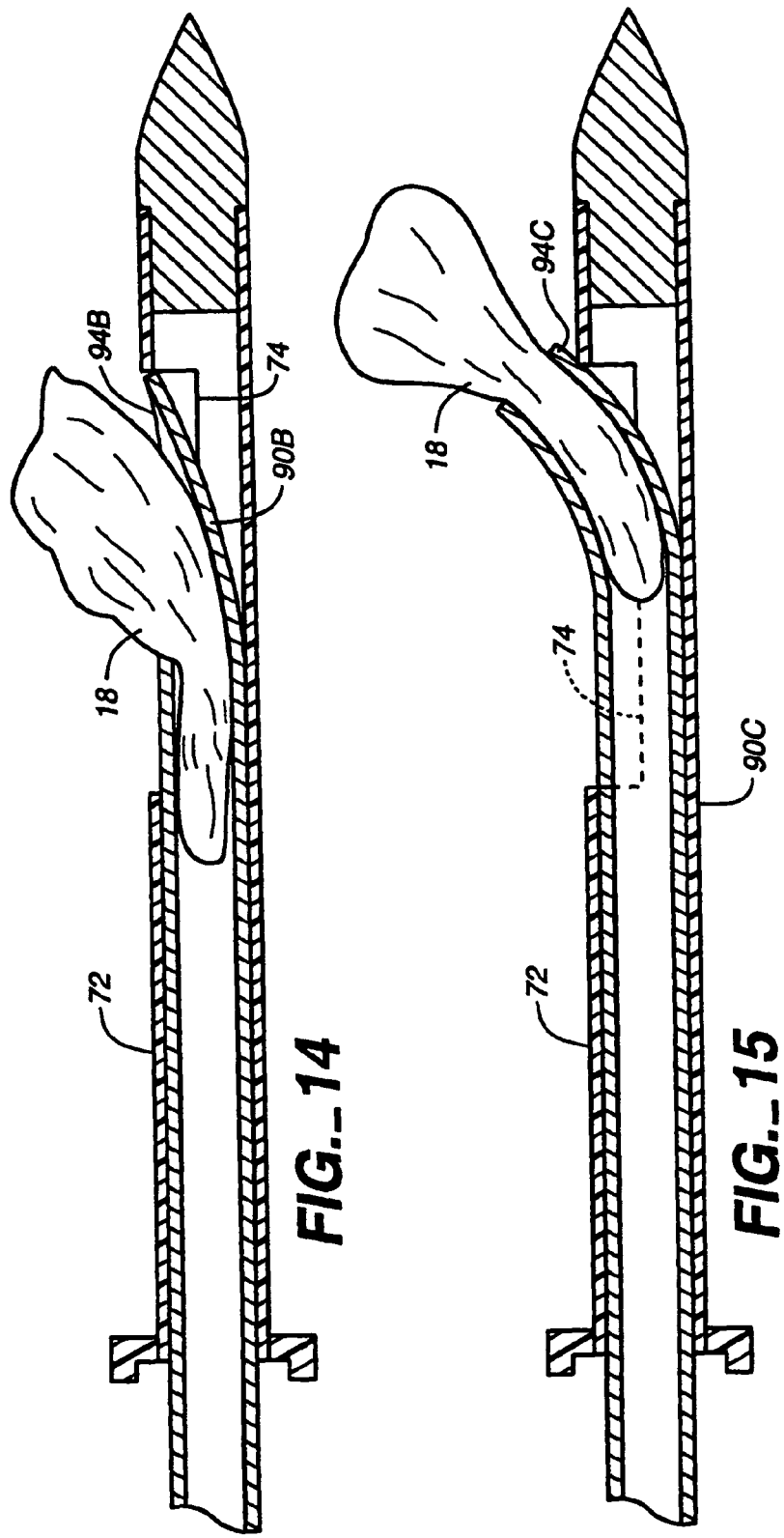

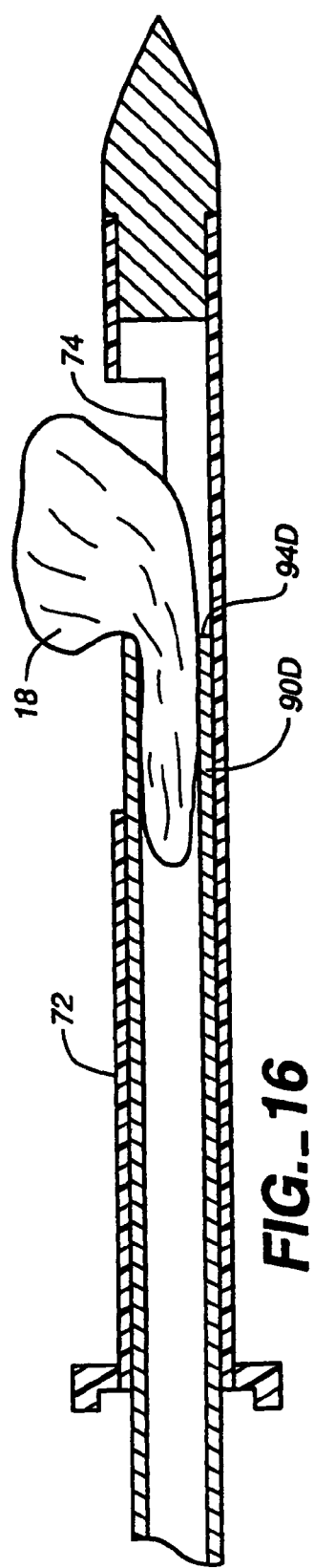

DEVICE AND METHOD FOR FACILITATING HEMOSTASIS OF A BIOPSY TRACT

This application is a continuation of U.S. application Ser. No. 09/960,389, filed Sep. 24, 2001, now U.S. Pat. No. 6,846,320, which is a continuation of U.S. application Ser. No. 09/382,160, filed Aug. 24, 1999, now abandoned, which is a continuation-in-part of U.S. application Ser. No. 09/247,880, filed Feb. 10, 1999, now U.S. Pat. No. 6,086,607, which is a continuation-in-part of U.S. application Ser. No. 09/071,670, filed May 1, 1998, now U.S. Pat. No. 6,071,301, each of which is incorporated herein by reference in its entirety.

BACKGROUND OF THE INVENTION

1. Field of the Invention

The invention relates to a wound closure device, and more particularly, the invention relates to a device and method for facilitating hemostasis of a biopsy site or other puncture wound by injection of an absorbable sponge.

2. Brief Description of the Related Art

Percutaneous needle biopsy of solid organs is one of the most common interventional medical procedures. Millions of percutaneous needle biopsies are performed annually in the United States and throughout the world. Percutaneous biopsy is a safe procedure which has supplanted surgical biopsy for many indications, such as skin, liver, and breast biopsy.

Possible complications of needle biopsy include bleeding at the biopsy site. The amount of bleeding is related to a number of factors including needle size, tissue sample size, patient's coagulation status, and the location of the biopsy site. Vascular organs such as the liver, a common biopsy target, may bleed significantly after needle biopsy. To minimize bleeding from a biopsy site, small-gauge needles are typically used. Small gauge needles, however, produce less satisfactory biopsy specimens but frequently are favored over larger bored needles because of their perceived safety. In order to minimize the chance of internal bleeding after biopsy, external pressure is applied for a substantial period of time.

Sterile sponges, such as Gelfoam, are prepared in dry sterile sheets which are used as packing material during surgery for control of bleeding. The sponge sheets are left in the surgical site after surgery to stop bleeding and are absorbed by the body in 1 to 6 weeks. A number of techniques have used these absorbable sterile sponge materials to plug a biopsy tract to minimize or prevent bleeding. The absorbable sponge provides a mechanical blockage of the tract, encourages clotting, and minimizes bleeding though the biopsy tract. Despite the advantages of using absorbable sponge to plug a biopsy tract this technique has not achieved widespread use because of difficulty in preparing and delivering the dry sponge material into the biopsy tract.

One example of a biopsy wound closure device using an implantable sponge is described in U.S. Pat. No. 5,388,588. According to this patent, a circular sponge of an absorbable foam material is precut and inserted into a biopsy site by an applicator rod having the sponge positioned on the end. Once the sponge is implanted, the sponge absorbs blood and swells to fill the tract preventing further bleeding at the biopsy site. However, the sponge is difficult to deliver and expands slowly once delivered. In addition, this delivery method can only deliver a sponge of a limited size which provides less local compression than desired and may incompletely fill the target site. Further, bleeding may continue along sections of the biopsy tract where no sponge has been delivered.

Accordingly, it would be desirable to provide a device and method which will permit the delivery of an absorbable sponge to a biopsy tract in a simple and reliable manner.

Breast biopsy devices are generally used to take multiple subcutaneous biopsies of breast tissue and for removing lesions without having to reinsert an instrument into the patient for each tissue sample. Examples of breast biopsy devices are described in U.S. Pat. Nos. 5,775,333; 5,769,086; and 5,649,547. These devices, commonly known as mammatomes, include a disposable cannula with a sharp distal tip and a side port adjacent the distal end. A tubular inner cutter blade extends through the cannula to cut tissue which extends into the side port. Using different rotational orientations of the cannula, biopsy cores can be taken at different radial locations within the tissue to be sampled. These devices provide an advantage over conventional needle biopsy in that significant amounts of tissue can be removed. However, the increased amount of tissue removed increases the potential for bleeding, hematoma, echimosis, and the like. Accordingly, it would be desirable to provide a device and method which will permit the delivery of an absorbable sponge to a breast biopsy site to facilitate hemostasis.

In addition, after a breast biopsy, an implantable marking device such as the one disclosed in U.S. Pat. No. 5,902,310 may be placed at the biopsy site so the site can be located for a follow up surgical procedure. This marking device is a metallic, radiopaque marker clip which is delivered by a wand through the biopsy cannula. However, if follow up surgery is not required the clip remains within the patient permanently. The permanently implanted clips can prove problematic, as they can migrate. Accordingly, it would be desirable to provide a radiopaque marker for locating a biopsy site which is formed of an absorbable material.

SUMMARY OF THE INVENTION

The present invention relates to a device and method for facilitating hemostasis of a biopsy tract or other puncture wound by injecting an absorbable sponge. More particularly, the system according to the present invention allows delivery of a hydrated absorbable sponge to a breast biopsy site through a biopsy cannula.

In accordance with one aspect of the present invention, a system for injecting a sponge into tissue includes a catheter having a closed distal end and a side port adjacent the distal end for delivering a pledget of sponge material in a hydrated state to the tissue and an adaptor connected to the catheter for hydrating and delivering the pledget to the catheter, the adaptor having a tapered lumen with a large diameter proximal end and a small diameter distal end, wherein the small diameter distal end is connected to the cannula.

In accordance with another aspect of the present invention, a method of delivering an absorbable radiopaque marker to a breast biopsy site includes the steps of removing tissue from a breast biopsy site through a cannula inserted to the breast biopsy site and delivering an absorbable radiopaque marker through the cannula to the breast biopsy site.

In accordance with a further aspect of the present invention, a method of facilitating hemostasis of a breast biopsy site includes the steps of removing tissue from a breast biopsy site through a side port of a cannula inserted to the breast biopsy site and delivering a sponge pledget through the side port of the cannula to the breast biopsy site.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a perspective view of a punch for forming pledgets;

FIG. 2 is a side cross sectional view of an adaptor for delivery of a pledget to a biopsy needle or cannula;

FIG. 3 is a side cross sectional view of a syringe for connection to the adaptor;

FIG. 4 is a side cross sectional view of an adaptor and syringe combination with a pledget positioned within the adaptor;

FIG. 5 is a side cross sectional view of an adaptor and syringe combination of FIG. 4 in which the pledget has been hydrated and moved into a small diameter end of the adaptor;

FIG. 6 is a side cross sectional view of the loaded adaptor and syringe combination in preparation for connection to a biopsy needle, catheter, or cannula;

FIG. 7 is a side cross sectional view of an alternative embodiment of a loaded adaptor connected to a biopsy needle and syringe;

FIG. 8 is a perspective view of an apparatus for collection of breast biopsies;

FIG. 9 is a cross sectional view of the breast biopsy apparatus of FIG. 8;

FIG. 10 is a side cross sectional view of a breast biopsy cannula and a delivery catheter for delivery of a pledget to the breast biopsy site;

FIG. 11 is a side cross sectional view of the breast biopsy cannula, a delivery catheter, and an adaptor for delivery of a pledget to the breast biopsy site;

FIG. 12 is a side cross sectional view of the delivery catheter and a sleeve for staging the pledget in the catheter;

FIG. 13 is a side cross sectional view of a breast biopsy cannula and second embodiment of a delivery catheter;

FIG. 14 is a side cross sectional view of a breast biopsy cannula and a third embodiment of a delivery catheter;

FIG. 15 is a side cross sectional view of a breast biopsy cannula and a fourth embodiment of a delivery catheter; and FIG. 16 is a side cross sectional view of a breast biopsy cannula and a fifth embodiment of a delivery catheter.

DETAILED DESCRIPTION OF THE PREFERRED EMBODIMENTS

The system of the present invention delivers an absorbable sponge material in a hydrated state to facilitate hemostasis of a biopsy tract or other puncture wound in a simple and safe manner. The apparatus for delivering a hydrated absorbable sponge will be described below in connection with treatment of a biopsy tract after a percutaneous needle biopsy. However, the invention may be used for facilitating hemostasis of other types of puncture wounds or tissue access tracts to prevent bleeding of these wounds. The apparatus described with respect to FIGS. 1-7 is used for delivery of sponge material into all types of biopsy tracts in many different organs and tissues. The apparatus described with respect to FIGS. 8-12 is particularly designed for delivery of sponge material after biopsy with a breast biopsy device commonly known as a mammatome, however, this system can also be used for treatment of other biopsy sites and other types of wounds.

The system for facilitating hemostasis of the biopsy tract includes a punch 10 for cutting a pledget 18 of absorbable sponge material from a sheet of this material, an adaptor 12 for delivering the pledget to a biopsy needle 16, and a syringe 14 for hydrating and injecting the pledget. The adaptor 12 allows a relatively large pledget of absorbable sponge material to be compressed and inserted into the biopsy tract in a hydrated state. The absorbable sponge material for use in facilitating hemostasis may be any absorbable sponge which is capable of deforming upon hydration to be delivered by fluid pressure into or through a biopsy needle or other cannula.

Prior to discussing the present invention in further detail, the following terms are defined:

"Pledget" means a piece of sponge of a generally elongated shape having a size which allows injection in a hydrated state through a biopsy needle or other cannula.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which when implanted within a human or other mammalian body is absorbed by the body.

"Hydrate" means to partially or fully saturate with a fluid, such as, saline, water, contrast agent, thrombin, therapeutic agent, or the like.

"Kneading" of the absorbable sponge material means both dry and wet manipulation of sponge material which compresses, enlarges, or changes the shape of the sponge material causing the sponge material to have improved expansion response.

FIG. 1 illustrates one example of a punch 10, also called a dye cutter, for cutting an absorbable sponge sheet 20 into pledgets 18 of an appropriate size for delivery to a biopsy tract. The punch 10 includes a rectangular blade 22 fixed to a plate 24 having a handle 26. The punch 10 is pressed down onto a flat sheet 20 of commercially available absorbable sponge to cut the pledget 18 of an appropriate size. In addition to the punch 10 illustrated in FIG. 1 other cutting devices, such as, a scissor type hand punch, an automatic punching machine, or a templet and knife may be used for preparation of the pledget 18.

FIG. 2 shows the adaptor 12 according to the present invention in which the pledget 18 is placed for hydration and for delivery through the biopsy needle 16. The adaptor 12 allows pieces of absorbable sponge material with relatively large cross sections to be easily delivered through a biopsy needle 16 with a much smaller cross section. The adaptor 12 also functions to remove air from the pledget 18.

The adaptor 12 which delivers the hydrated pledget 18 to the needle 16 includes a first end 30 having an annular lip 32 or female luer fitting for connection to the syringe 14. A second end 34 of the adaptor 12 has a male luer fitting 36 for connection to a biopsy needle 16 or other cannula. The luer fitting 36 includes a tapered external surface 38 and a retaining ring 40 with internal threads for receiving an annular lip of the biopsy needle. The adaptor 12 has an internal lumen with a first diameter $D_1$ at the first end 30 and a second diameter $D_2$ at the second end 34. Between the first and second ends of the adaptor 12 a tapered section 42 of the adaptor provides a funnel for compressing the hydrated pledget 18 prior to injection through the biopsy needle 16 and needle hub 28.

The adaptor 12 may be formed in any known manner such as by molding from a plastic material. Preferably, the adaptor 12 is transparent so that the pledget 18 can be viewed through the adaptor and the user can visually monitor when the pledget is loaded within the adaptor and when the pledget has been delivered into the needle. The adaptor lumen may be provided with a friction reducing coating for improved delivery. The delivery fluid also reduces friction for improved delivery by wetting the exterior surface of the pledget 18.

The syringe 14 includes a male luer fitting 46, a fluid chamber 48, and a plunger 50. The first end 30 of the adaptor 12 is connectable to the luer fitting 46 of the conventional syringe 14. The syringe 14 may be provided with a spring 52 for automatic filling of the syringe 14 with a predetermined volume of fluid. Alternatively, the syringe may include a threaded syringe plunger, as shown in FIG. 7, for accurate injection of small quantities of fluid. The syringe volume will vary depending on the amount of fluid needed for hydration and delivery of the pledget 18 through the biopsy needle 16.

A biopsy needle 16 for use with the present invention is preferably a co-axial biopsy needle, such as a bi-axial or a tri-axial biopsy needle. A co-axial biopsy needle includes an outer needle or cannula through which a tissue sample is removed with a tissue scoop or other biopsy instrument. Once the tissue sample has been removed, the outer cannula remains in the patient as illustrated in FIG. 6. Although the cannula 16 for delivery of the sponge pledget has been described as a biopsy needle, the cannula may be a catheter, sheath, or any other type of cannula.

The method of facilitating hemostasis of a biopsy tract will be described with reference to FIGS. 4-6. FIG. 4 shows the loading and hydration of the pledget 18 within the adaptor 12. A pledget 18 is cut as described above and placed within the adaptor 12 from the first end 30 of the adaptor. The syringe 14 is filled with a predetermined amount of fluid, such as saline, and is connected to the first end 30 of the adaptor 12 by the luer fitting 46. The plunger 50 of the syringe 14 is then depressed slowly causing fluid to pass into the adaptor 12, hydrating the pledget 18, and filling the adaptor with a column of fluid. Care should be taken to inject the fluid slowly to prevent the pledget from being ejected out of the second end 34 of the adaptor. Preferably, the user waits a few seconds once the fluid is injected into the adaptor 12 until the pledget 18 is adequately hydrated creating a lubricous surface on the pledget. The pledget 18 may expand within the adaptor to fill or nearly fill the lumen of the adaptor. The adaptor 12 with the pledget 18 hydrated within the proximal end is ready to inject the pledget into a biopsy tract to facilitate hemostasis within the biopsy tract. The adaptor 12 may be loaded prior to beginning the biopsy procedure.

According to one embodiment of the adaptor illustrated in FIG. 5, vent holes 44 extend through the side walls of the adaptor 12 adjacent the second end 34 for venting fluid during loading of the pledget 18. As illustrated in FIG. 5, the user places a finger over the second end 34 of the adaptor 12 to prevent the pledget from exiting the adaptor. The plunger 50 of the syringe 14 is then depressed slowly causing fluid to pass into the adaptor 12 and hydrate the pledget. Preferably, the user waits a few seconds once the fluid is injected into the adaptor 12 until the pledget 18 is hydrated. Once the pledget 18 is hydrated, additional fluid is then injected quickly into the adaptor 12 to move the pledget 18 from the first end 30 of the adaptor towards the second end 34 of the adaptor. As the pledget 18 is compressed by the tapered section 42 of the adaptor 12 air and fluid are allowed to escape from the adaptor through the vent holes 44. Once the pledget 18 has been moved into the position illustrated in FIG. 5 adjacent the second end 34, fluid injection is halted. The adaptor 12 with the hydrated pledget 18 within the distal end is ready to insert the pledget through a biopsy needle to facilitate hemostasis within the biopsy tract.

As an alternative to placement of a finger at the distal end of the adaptor 12 during advancement of the pledget 18 through the tapered section 42, a removable cap may be used. Further, the vent holes 44 may be omitted and a screen or a cap having a screen may be used to allow fluid to pass through the screen while the screen prevents the pledget 18 from being ejected.

The pledget 18 may be positioned within the adaptor 12 for delivery to the biopsy cannula 16 either in the proximal position illustrated in FIG. 4 or in the distal position illustrated in FIG. 5. With either of these pledget positions, the procedure for delivery of the pledget to the biopsy tract is described below.

After the tissue samples have been taken, the outer sheath of the biopsy needle 16 through which the biopsy has been taken is maintained in place within the biopsy tract, as shown in FIG. 6. The biopsy needle 16 provides pre-established targeting of the delivery site for delivery of the absorbable sponge pledget 18 and eliminates the uncertainty of re-access. The luer fitting 36 of the adaptor 12 is connected to the biopsy needle hub 28, as illustrated in FIG. 6. The biopsy needle 16 is withdrawn a short distance, such as about 1 to 20 mm, along the biopsy tract to provide space for the pledget 18 to be received in the biopsy tract. Additional fluid is then rapidly injected by the syringe to move the pledget 18 into the biopsy needle 16 to the biopsy site.

When the adaptor lumen has been blocked by the hydrated pledget 18 which has swelled within the adaptor, injection of additional fluid will push the pledget through the tapered section 42 of the adaptor. If the adaptor lumen has not been entirely blocked by the pledget 18, the venturi effect will help draw the pledget through the tapered section 42 of the adaptor. After the pledget 18 is moved to the biopsy needle 16, the pledget 18 is then delivered from the needle 16 to the biopsy tract by rapid injection of additional fluid by the syringe 14. The hydrated pledget 18 quickly expands upon delivery to fill the available space in the biopsy tract to facilitate hemostasis and provide localized compression.

In some instances it may be desirable to deliver multiple pledgets in spaced apart positions along the biopsy tract, particularly for a long biopsy tract. For delivery of additional pledgets, the biopsy needle 16 is retracted a distance sufficient to provide a space to accommodate an additional pledget 18 and the injection procedure described above is repeated for the additional pledget(s). For a particularly large biopsy site or cavity, additional pledgets 18 may be injected beside an initially injected pledget until the cavity is filled.

As illustrated in the cross sectional view of FIG. 7, one example of a needle hub 28 has an interior diameter $D_3$ which is larger than the diameter $D_2$ at the distal end 36 of the adaptor 12. The large internal diameter needle hub 28 allows the hydrated pledget 18 which has been compressed by the tapered section 42 of the adaptor to expand in the needle hub before being compressed again into the needle lumen. This compression and enlargement of the hydrated absorbable sponge material, does not adversely effect the pledget delivery and in fact improves the expansion response of some delivered sponge materials as will be discussed in further detail below.

A smooth tapered transition between the lumen of the needle hub 28 and the needle lumen helps to provide for easy injection of the pledget 18. However, needles having internal steps between the needle hub 28 and the needle 16 have been used and the pledget 18 is still injected successfully. According to an alternative embodiment of the invention, the needle hub 28 may be designed to have a inner diameter approximately the same as the inner diameter $D_2$ at the distal end 36 of the adaptor.

Preferably, specific measured doses of fluid are used to achieve each of the steps of the treatment procedure depending on the pledget size and the dimensions of the adaptor 12, the needle 16, and the needle hub 28. The pledget 18 should be completely delivered into the biopsy tract by the fluid and only a minimal amount of extraneous fluid should be delivered. For example, the pledget 18, once inside the needle, may be delivered with about 0.02 to 1.5 ml of fluid depending on the size of the needle 16 used. Injection of larger amounts of fluid may distend the biopsy tract or displace the pledget within the organ.

According to one example, a pledget 18 having a size of approximately 20 mm by 2 mm cut from a sheet of commercially available Gelfoam having a thickness of approximately 1.5 mm can be hydrated and injected through a standard 18 gauge, approximately 15 cm long biopsy needle with approximately 0.9 ml of fluid. An adaptor according to this example has a first diameter $D_1$ of about 0.38 cm, a second diameter $D_2$ of about 0.14 cm, a total length of about 3.80 cm, and a taper angle of about 45°. About 0.3 ml of fluid is injected slowly to hydrate the pledget 18 and fill the adaptor with a column of fluid. Approximately 0.3 ml of fluid is then injected to load the pledget 18 from the adaptor 12 into the biopsy needle 16. Finally, about 0.3 ml of fluid is injected to deliver the pledget 18 into the biopsy tract. Loading of the pledget from the adaptor 12 into the needle 16 and delivery from the needle to the biopsy tract can be combined in one step by delivery of approximately 0.6 ml. Accurate and complete injection of the pledget with a minimum amount of extraneous fluid is achieved by this volumetric injection technique.

An alternative embodiment of the delivery system is illustrated in FIG. 7 in which an adaptor 12 is provided with a pressure indicator 64 to monitor pledget injection. Preferably, the pressure indicator 64 is removably attached at a luer fitting 66 provided on a side of the adaptor 12. The pressure indicator 64 includes a pressure dome 68 movable from the convex shaped extended position illustrated in FIG. 7 to a flat position depending on the pressure inside the adaptor 12. Internal pressure within the biopsy needle 16, the adaptor 12, and the syringe 14 will drop as the pledget 18 is extruded from the biopsy needle into the biopsy tract. This causes the pressure dome 68 to move from the convex position illustrated in FIG. 7 to a flat position, indicating that pledget delivery is complete.

The particular size and shape of the adaptor 12 according to the invention may vary depending on the size of biopsy needle, the tissue sample size, and the size of pledget to be delivered. One example of an adaptor for delivery of an absorbable sponge pledget 18 through an approximately 18 gauge biopsy needle has a first adaptor diameter $D_1$ of about 0.25 cm or greater, preferably about 0.30 to 0.80 cm and a second adaptor diameter $D_2$ of about 0.25 cm or less, preferably, about 0.05 to 0.23 cm. An angle made by a wall of the tapered section 42 with a longitudinal axis of the adaptor 12a may vary from about 50 to 90°, but is preferably between about 30° and 60°. The tapered section 42 is illustrated with a substantially planar interior surface, when shown in cross section. However, the tapered section 42 may also have a convex or concave surface in cross section. The dimensions described for the adaptor 12 are appropriate for use with an approximately 18 gauge biopsy needle commonly used for liver biopsies. For some of the much larger biopsy needles or cannulas used for skin or breast biopsies the adaptor dimensions would be scaled up accordingly.

One type of absorbable sponge material which is acceptable for use in the present invention is Gelfoam, manufactured by the Pharmacia & Upjohn Company. Gelfoam is a porous, pliable, cross-linked gelatin material and is available commercially in sheet form as pre-compressed or non-compressed sponge. The material may be provided preformed as a pledget 18 or may be cut with a punch 10, or a stencil or template and knife to form a pledget as described above. Once hydrated, the pledget 18 can be easily compressed to fit into a lumen having a smaller cross sectional area than the original cross sectional area of the pledget. Additionally, the kneading of the hydrated pledget 18 during delivery encourages air trapped within the Gelfoam to be expelled and replaced with fluid, allowing rapid expansion upon delivery. When a pledget 18 of a pre-compressed Gelfoam is hydrated and kneaded (expelling air) during delivery, the pledget will have the absorption capacity to rapidly expand to many times (e.g., 3 or more times) its original dry volume upon delivery. When a pledget 18 of the non-compressed Gelfoam is hydrated and kneaded (expelling air) during delivery, the pledget will have the absorption capacity to rapidly expand to its original dry volume upon delivery. These properties make the Gelfoam sponge material particularly useful for facilitating hemostasis of biopsy sites.

Abrupt lumen diameter changes within or between the adaptor 12 or the needle 16 will improve "kneading" of the absorbable sponge material improving hydration of the absorbable sponge material thereby improving the expansion properties of the hydrated delivered absorbable sponge. Enlarged, recessed, or irregular areas in the lumen of the adaptor may be provided to impart additional kneading action to the absorbable sponge material further improving expansion properties of the sponge.

When delivering a pledget 18 of absorbable sponge material, it is important to deliver a desired amount of the sponge material using a minimum amount of fluid. Some devices and methods which allow the delivery of sponge material with a minimum amount of fluid include the use of a pledget configuration with an enlarged proximal end, the use of a vent cap for staging of the pledget, and the use of a plunger to deliver the pledget while withdrawing the biopsy needle during delivery.

FIG. 8 shows an apparatus for performing breast biopsies commonly known as a mammatome system 70. The mammatome system 70 includes a biopsy cannula 72 having a tissue receiving side port 74 and an inner cutter 76 which is longitudinally movable within the biopsy cannula. The inner cutter 76 functions as the biopsy cutter or punch and has a circular cutting blade 78 at a distal end. In use, the mammatome system 70 is inserted into tissue such that the side port 74 of the cannula 72 opens within the tissue to be sampled. The inner cutter 76 is then advanced to cut through a portion of tissue which extends into the side port 74. The cutter 76 may be rotated while it is advanced to improve cutting. The sample is then removed and the cannula 72 may be rotated to take additional samples at different rotational orientations.

FIG. 9 is a cross sectional side view of the cannula 72 and the inner cutter 76 of FIG. 8. As shown in FIG. 9, the cannula 72 may include an indexing wheel 82 for rotation of the cannula after each sample has been taken. The taking of multiple samples by rotation of the biopsy cannula 72 and repeated sampling at different rotational orientations results in significant amounts of tissue being removed from the tissue site. The large amount of tissue removed increases the potential for bleeding, hematoma, echimosis, etc. Thus, the delivery of the absorbable sponge pledget 18 according to the present invention is particularly advantageous in breast biopsy applications. Although the absorbable sponge pledget can be delivered directly through the biopsy cannula 72 with an adaptor 12 similar to that shown in FIG. 2, two alternative systems for delivery of a pledget are shown in FIGS. 10 and 11.

FIG. 10 illustrates the biopsy cannula 72 and a delivery catheter 90 configured to deliver one or more absorbable sponge pledgets through the cannula to the biopsy site. The delivery catheter 90 includes a closed distal end 92, a side port 94, a tapered section 96, and an enlarged proximal portion 98 for receiving the pledget. The side port 94 of the delivery catheter 90 is arranged to delivery the pledget through the side port 74 of the cannula 72. Accordingly, the catheter side port 94 is preferably the same size or smaller than the side port 74 of the cannula 72. The delivery catheter 90 also includes a proximal fitting 100 for connection to a syringe and an indexing element 102. The indexing element 102 engages with the indexing wheel 82 on the cannula 72 to align the side ports 74, 94 of the cannula and catheter. Alternatively, alignment may be performed by aligning a marker on the catheter 90 with a corresponding marker on the cannula 72. Another system for alignment of the cannula 72 and the delivery catheter may include one or more detents and corresponding recesses or grooves in the shafts of the cannula and catheter. In the alternative, the outer surface of the catheter 90 could be configured to engage the inner surface of the cannula 72 to resist relative movement or displacement between the catheter 90 and the cannula 72.

The delivery catheter 90 operates in the manner described above with respect to the embodiments of FIGS. 1-7 to allow a large amount of hydrated sponge material in the form of a pledget to be delivery to the biopsy site to facilitate hemostasis. In order to fill a relatively large biopsy site where multiple tissue samples have been taken in a radial pattern, the biopsy cannula 72 is rotated and additional pledgets are delivered to the biopsy site at different radial locations.

FIG. 11 shows an alternative system for delivering one or more pledgets through the biopsy cannula 72 of a mammatome system 70 to a biopsy site. This system includes a delivery catheter 110 and an adaptor 112 which may be similar to the adaptor 12 described above with respect to the embodiments of FIGS. 1-7. The delivery catheter 110 includes a plugged distal end 114, a side port 116 for delivery of the pledget, a proximal fitting 118, and an indexing element 120. The pledget is delivered from the adaptor 112, through the delivery catheter 110 fitted in the biopsy cannula 72, to the biopsy site. The adaptor 112 is connectable to the delivery catheter 110 by a distal fitting 124. The adaptor 112 has a tapered section 126 for compressing the pledget, a proximal portion 128 for receiving the pledget, and a proximal fitting 130 for connecting the adaptor to a syringe.

In use, the delivery catheter 110 and adaptor 112 system of FIG. 11 can be used to deliver a plurality of pledgets quickly to a breast biopsy site. With this system, multiple adaptors 112 may be preloaded with hydrated pledgets as described above. These adaptors may be sequentially attached to the delivery catheter 110 to deliver the multiple pledgets at different rotational orientations.

FIG. 12 illustrates a sleeve 140 for staging the pledget at a preferred position within the delivery catheter 110 prior to insertion of the delivery catheter into the biopsy cannula 72 for delivery of the pledget to the biopsy site. The sleeve 140 is configured to receive a distal portion of the delivery catheter 90, 110 having the side port 116. The fit and/or resilience between the sleeve 140 and the catheter 110 allows fluid to pass out or be vented from the catheter and sleeve as the pledget moves to a position adjacent the side port 116, but prevents the pledget from being expelled. The sleeve 140 is then removed and the delivery catheter 110 is placed into the biopsy cannula 72 for delivery of the pledget to the biopsy site. This positioning of the pledget in the delivery catheter 110 prior to insertion of the catheter into the cannula 72 decreases an amount of fluid which is delivered to the biopsy site along with the pledget.

FIGS. 13-16 illustrate four alternative embodiments for the distal end of the delivery catheter 90A-90D. The delivery catheter of FIG. 13 has a blunt distal end 92A and a sided port 94A. A pledget 18 of absorbable sponge material is delivered through a lumen of the delivery catheter 90A and out of the side port 94A by a column of fluid. Preferably, a diameter of the side port 94A is approximately the same as a diameter of the delivery catheter lumen. The catheter lumen can either end at the location of the side port 94 or can extend to the plugged distal end 92A of the catheter. The relatively small side port 94A of this embodiment prevents the pledget material from becoming caught on the side port as the biopsy cannula 72 and delivery catheter 90A are withdrawn from the biopsy site.

FIG. 14 illustrates an alternative embodiment of a delivery catheter 90B having a side port 94B for delivering a pledget out of the side port 74 of the biopsy cannula 72. The distal end of the delivery catheter 90B is curved and cut off at an angle which is substantially parallel with a side wall of the biopsy cannula 72. The curved configuration of the delivery catheter distal end shown in FIG. 14 prevents the absorbable sponge material from becoming caught as the biopsy cannula is removed from the biopsy site.

FIG. 15 illustrates a further alternative embodiment of a delivery catheter 90C having a side port 94C which is formed by bending a distal end of the delivery catheter so that it extends out through the side port 74 of biopsy cannula 72. The distal end of the delivery catheter 90C may be cut at 90° or at an angle as illustrated in FIG. 15. According to the embodiment of the delivery catheter 90C of FIG. 15, the distal end of the delivery catheter extends outside of the biopsy cannula 72 for delivery of the pledget 18 into the biopsy site.

Finally, FIG. 16 illustrates a further alternative embodiment of a delivery catheter 90D having a blunt distal end delivery port 94D. Although the delivery catheter 90D of FIG. 16 provides a simplified delivery system for delivery of the pledget 18, this system provides increased risk of dislodging the pledget 18 from the biopsy site upon withdrawal of the biopsy cannula 72 due to the possibility of the pledget becoming caught on a trailing edge of the cannula side port 74.

Each of the delivery catheters 90, 90A-90D may be provided with staging systems such as the sleeve described above with respect to FIG. 12. The staging systems for positioning the pledget at a preferred position within the delivery catheter prior to insertion of the delivery catheter into the biopsy cannula 72 may include either a sleeve as described in FIG. 12 or any one of a number of different configurations of vent caps which are described in U.S. patent application Ser. No. 09/247,880.

The delivery of the pledget(s) of sponge material to the breast biopsy site may also be used to provide a temporary or permanent marker at the biopsy site for future location of the site for further surgery by delivery of a non-absorbable sponge material or a radiopaque sponge material. An absorbable sponge containing a contrasting agent (e.g, radiopaque agent) that can be introduced to a biopsy tract to permit identification of the site by fluoroscopy or other imaging techniques is described in U.S. patent application Ser. No. 09/335,452 filed on Jun. 17, 1999, which is incorporated herein by reference. The radiopaque pledget provides the ability to locate the biopsy site for a period of time following the biopsy procedure so that the site can be easily located if additional surgery is necessary. If surgery is not necessary, the pledget will be absorbed over time and will not migrate within the breast or interfere with later visualization as with the permanent metal clips described in U.S. Pat. No. 5,902,310.

The absorbable sponge material may also be used to deliver medicaments to the biopsy site.

Although the invention is primarily intended for delivery of absorbable sponge, non-absorbable sponge may also be delivered with the devices, systems, and methods of the present invention. A non-absorbable sponge may be desirable where it will be necessary to locate the biopsy site or tract after the procedure.

Although the pledget 18 has been shown and described as having a rectangular cross section, pledgets of other shapes may also be used. For example, the pledget may be preformed in any shape, such as with a rectangular or circular cross section or may be rolled from a thin sheet of absorbable sponge material. The pledget 18 may have a multi-sided cross section, a star shaped cross section, or a folded cross section and may have through or blind holes formed in the dry pledget. In addition, the pledget size and shape can be matched to the size and shape of a particular delivery site. Pledget shapes having greater surface area provided by features such as fins provide faster hydration.

The continuous structure of the absorbable sponge pledget 18 provides more secure and reliable placement than a paste or liquid and can even facilitate partial withdrawal, removal, or movement of the delivered pledget.

Although biopsy is most commonly performed by biopsy needle, biopsy may also be performed through other cannulas, such as catheters, long needles, endoscopes, or the like. The treatment procedure according to the present invention can be used for facilitating hemostasis of puncture wounds through different types of cannulas including needles, catheters, endoscopes, and the like. In addition, the treatment procedure and systems according to the present invention may be used to deliver absorbable or non-absorbable sponge for other therapies. For example, sponge may be delivered for cosmetic or reconstructive bulking or for temporary or permanent intravascular embolization.

The absorbable sponge pledget 18 may be used to deliver a beneficial agent, such as contrast agent, thrombin, radiation treatment, or the like. The pledget can also be used to deliver therapeutic agents, such as radioactive isotopes for localized treatment of tumors, anti-cancer agents, anti-metastatic agents, and the like. Examples of anti-cancer agents include 5-fluorouracil, cisplatin, prednisone, and others described in U.S. Pat. No. 4,619,913 which is incorporated herein by reference. The absorbable sponge pledget 18 may be pre-soaked with the beneficial agent for delivery to the biopsy tract. Alternatively, the pledget 18 may be hydrated with the beneficial liquid agent or the agent may be delivered to the pledget after the pledget is placed within the biopsy tract.

A pledget formed of commercially available Gelfoam material will be absorbed by the body within 1 to 6 weeks. However, the pledget material may be designed to provide different rates of absorption. For example, Gelfoam can be designed to be absorbed at different rates by varying the degree of cross-linking. Preferably, the pledget is designed to be absorbed in less than one month.

The treatment of a biopsy tract with a hydrated and injected pledget 18 of absorbable sponge to facilitate hemostasis provides substantial advantages in comfort over external pressure methods. In addition, the present invention also provides advantages over the insertion of an absorbable sponge material in a dry state with an applicator. In particular, the adaptor 12 allows a relatively large pledget to be compressed and inserted into the biopsy tract in a hydrated state. The injected pledget 18 conforms in shape quickly to the shape of the biopsy tract and immediately begins blocking blood flow. In contrast, a dry piece of sponge material must be cut to the particular size of the biopsy tract and does not swell to fill the tract until the blood has sufficiently saturated the sponge material which can take significantly longer and provides inadequate local compression.

While the invention has been described in detail with reference to the preferred embodiments thereof, it will be apparent to one skilled in the art that various changes and modifications can be made and equivalents employed, without departing from the present invention.

What is claimed is:

1. A method of delivering an absorbable radiopaque marker to a biopsy site comprising:
    inserting a cannula having a side port to a biopsy site such that tissue from the biopsy site extends into the side port;
    advancing a cutter disposed within the cannula through a portion of the tissue extending into the side port to capture a sample of the tissue;
    removing the cutter and the tissue sample from the cannula;
    introducing a delivery catheter into the cannula, the delivery catheter configured to deliver an absorbable radiopaque marker through the side port of the cannula to the biopsy site;
    delivering the absorbable radiopaque marker through a lumen of the delivery catheter and out of the side port of the cannula to the biopsy site, wherein the absorbable radiopaque marker is delivered by hydrating and compressing the absorbable radiopaque marker and injecting the marker by fluid pressure to the biopsy site; and
    withdrawing the cannula from the biopsy site, leaving the absorbable radiopaque marker at the biopsy site.

2. The method of claim 1, wherein the absorbable radiopaque marker is formed of an absorbable sponge material.

3. The method of claim 1, wherein the cannula remains in place at the biopsy site after removal of the tissue for delivery of the absorbable radiopaque marker.

4. The method of claim 1, wherein the absorbable radiopaque marker is formed of a hemostatic sponge material.

5. The method of claim 1, wherein the tissue is removed from a breast biopsy site.

6. The method of claim 1, wherein the delivery catheter has a blunt distal end and a side port.

7. The method of claim 6, wherein the side port has a diameter approximately equal to a diameter of the delivery catheter lumen.

8. The method of claim 6, wherein the step of delivering the absorbable radiopaque marker includes delivering the absorbable radiopaque marker through the side port of the delivery catheter.

9. The method of claim 1, wherein the delivery catheter has a distal end that is curved and cut off at an angle substantially parallel with a side wall of the cannula.

10. The method of claim 9, wherein the step of introducing the delivery catheter into the cannula includes aligning the distal end of the delivery catheter with the side wall of the cannula at the side port.

11. The method of claim 1, wherein the step of introducing the delivery catheter into the cannula includes extending a distal end of the delivery catheter through the side port of the cannula.

12. A method of delivering an absorbable radiopaque marker to a biopsy site comprising:
    inserting a biopsy cannula having a side port to a biopsy site;
    capturing and removing tissue from the biopsy site through the side port of the cannula;
    introducing a marker delivery catheter into the cannula to establish a delivery configuration, the delivery configuration adapted to deliver an absorbable radiopaque marker through the side port of the biopsy cannula to the biopsy site;

delivering the absorbable radiopaque marker through a lumen of the marker delivery catheter and out of the side port of the biopsy cannula to the biopsy site, wherein the absorbable radiopaque marker is delivered by hydrating and compressing the absorbable radiopaque marker and injecting the marker by fluid pressure to the biopsy site; and maintaining the marker delivery catheter in the delivery configuration while withdrawing the biopsy cannula from the biopsy site, leaving the absorbable radiopaque marker at the biopsy site;

wherein the delivery configuration prevents the absorbable radiopaque marker from becoming caught on the side port of the biopsy cannula as the biopsy cannula is withdrawn.

13. The method of claim 12, wherein the delivery catheter has a distal end that is curved and cut off at an angle substantially parallel with a side wall of the cannula.

14. The method of claim 13, wherein the step of introducing the delivery catheter into the cannula includes aligning the distal end of the delivery catheter with the side wall of the cannula at the side port.

15. A method of delivering an absorbable radiopaque marker to a biopsy site comprising:

inserting a cannula having a side port to a biopsy site;

capturing and removing tissue extending into the side port of the cannula from the biopsy site;

rotating the cannula at the biopsy site to capture and remove additional tissue through the side port of the cannula at a plurality of rotational orientations;

maintaining the cannula in place at the biopsy site after tissue is removed;

introducing a delivery catheter into the cannula, the delivery catheter adapted to deliver an absorbable radiopaque marker through the side port of the cannula to the biopsy site;

delivering the absorbable radiopaque marker through a lumen of the delivery catheter and out of the side port of the cannula to the biopsy site, wherein the absorbable radiopaque marker is delivered by hydrating and compressing the absorbable radiopaque marker and injecting the marker by fluid pressure to the biopsy site;

rotating the cannula at the biopsy site to deliver at least one additional absorbable radiopaque marker through the side port of the cannula to the biopsy site; and withdrawing the cannula from the biopsy site after delivering the absorbable radiopaque markers, leaving the absorbable radiopaque markers at the biopsy site.

16. The method of claim 15, wherein the delivery catheter has a distal end that is curved and cut off at an angle substantially parallel with a side wall of the cannula.

17. The method of claim 16, wherein the step of introducing the delivery catheter into the cannula includes aligning the distal end of the delivery catheter with the side wall of the cannula at the side port.

* * * * *